United States Patent [19]

Moss

[11] Patent Number: 5,536,255
[45] Date of Patent: Jul. 16, 1996

[54] DILATOR/INTRODUCER APPARATUS FOR PERCUTANEOUS GASTROSTOMY

[76] Inventor: Gerald Moss, R.D. #1, West Sand Lake, N.Y. 12196

[21] Appl. No.: 317,786

[22] Filed: Oct. 3, 1994

[51] Int. Cl.⁶ .................................................. A61M 25/01
[52] U.S. Cl. ............................................ 604/161; 604/165
[58] Field of Search ................................ 604/160, 161, 604/165, 177

[56] References Cited

U.S. PATENT DOCUMENTS

| | | |
|---|---|---|
| 4,077,412 | 3/1978 | Moossun . |
| 4,362,156 | 12/1982 | Feller, Jr. et al. .................. 604/177 |
| 4,377,165 | 3/1983 | Luther et al. . |
| 4,449,973 | 5/1984 | Luther . |
| 4,798,591 | 1/1989 | Okada .................................. 604/165 |
| 5,064,414 | 11/1991 | Revane ................................ 604/165 |
| 5,098,392 | 3/1992 | Fleischhacker et al. . |
| 5,139,486 | 8/1992 | Moss . |
| 5,141,497 | 8/1992 | Erskine ................................ 604/177 |
| 5,171,222 | 12/1992 | Euteneuer et al. .................. 604/160 |
| 5,186,712 | 2/1993 | Kelso et al. ......................... 604/177 |
| 5,195,978 | 3/1993 | Schiffer .............................. 604/161 |
| 5,221,263 | 6/1993 | Sinko et al. ......................... 604/161 |
| 5,261,887 | 11/1993 | Walker ............................... 604/161 |
| 5,304,142 | 4/1994 | Liebl et al. . |
| 5,324,269 | 6/1994 | Miraki ................................. 604/160 |
| 5,334,157 | 8/1994 | Klein et al ......................... 604/160 |
| 5,389,087 | 2/1995 | Miraki ................................. 604/160 |

*Primary Examiner*—Paul J. Hirsch
*Attorney, Agent, or Firm*—Schmeiser, Olsen & Watts

[57] ABSTRACT

A dilator/introducer apparatus incorporating a locking system for preventing the premature longitudinal separation of the first and second halves of a frangible-type introducer.

4 Claims, 3 Drawing Sheets

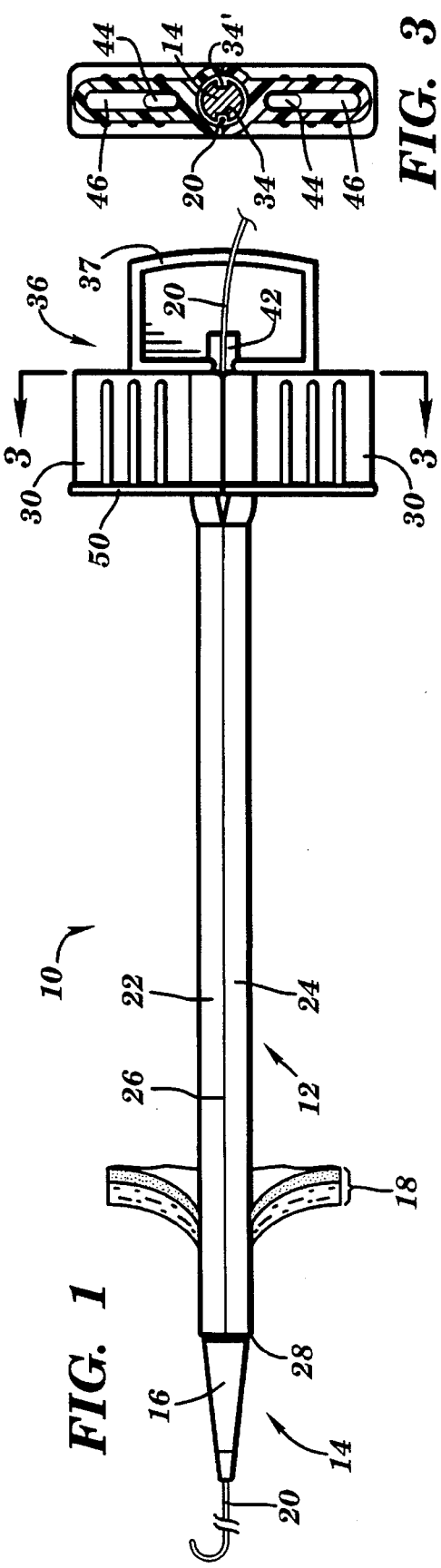

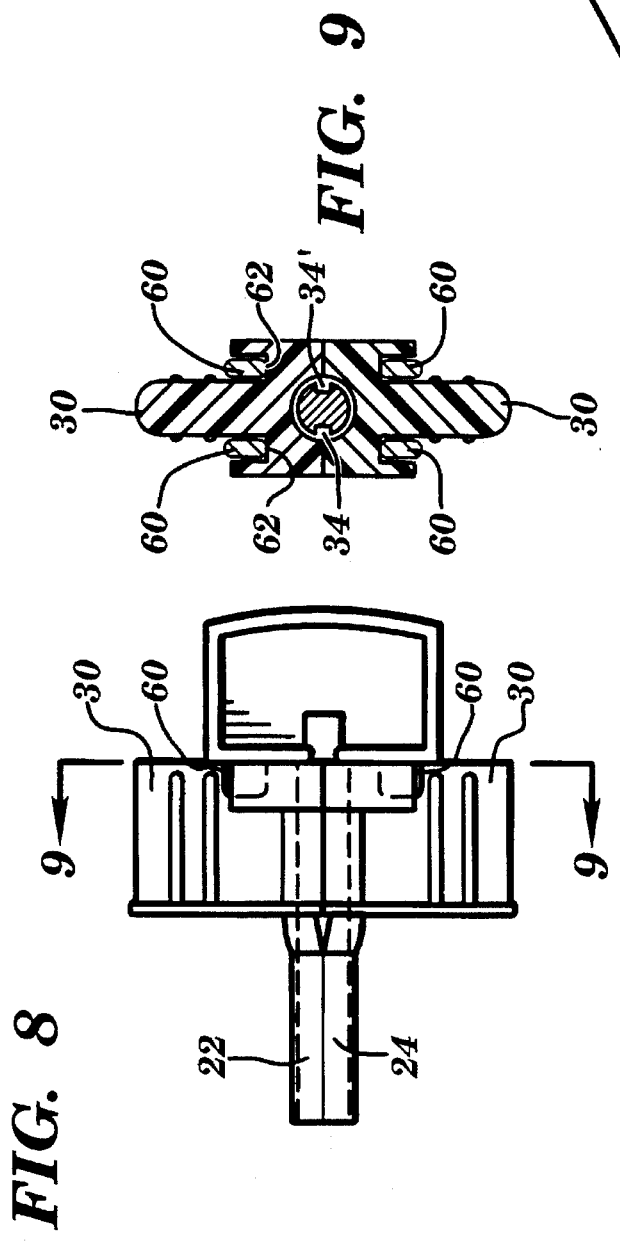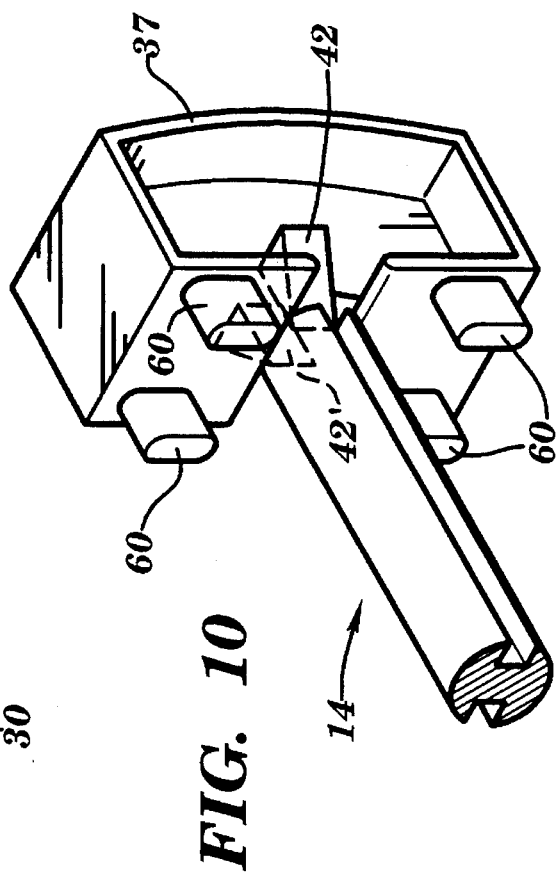

DILATOR/INTRODUCER APPARATUS FOR PERCUTANEOUS GASTROSTOMY

FIELD OF THE INVENTION

The present invention relates to a medical device for facilitating the placement of a catheter within a body and, more particularly, to an improved dilator/introducer apparatus for inserting a gastrointestinal aspirating and feeding tube into the gastrointestinal tract of a patient through the abdominal wall. The dilator/introducer apparatus incorporates a locking system for preventing the premature longitudinal separation of the first and second halves of a frangible-type introducer.

BACKGROUND OF THE INVENTION

During a percutaneous gastrostomy procedure, a gastrointestinal aspirating and feeding tube or other type of catheter is positioned within the gastrointestinal tract of a patient. Initially, the patient's stomach is percutaneously secured to the abdominal wall using "T" or "H"-shaped fasteners inserted into the stomach with a surgical fastener implantation device. Upon successful gastral securement, a thin metal or plastic "J"-wire is percutaneously introduced into the stomach through a hollow needle. If necessary, the distal end of the "J"-wire may be advanced to its required operational position within the gastrointestinal tract using the biopsy forceps of a gastroscope. A hollow dilator/introducer is subsequently displaced along the "J"-wire until it is percutaneously inserted into the patient, perforating the stomach.

Generally, a dilator/introducer is a multiple-piece device comprising a hollow dilator partially and slidably enclosed within an elongated introducer tube. The dilator includes a longitudinally extending interior passageway for receiving the "J"-wire therethrough, and a tapered, acicular end portion for perforating the abdominal and stomach walls of a patient. The elongated introducer is a frangible tube having first and second halves. The introducer includes a first end having an opening that is perpendicular to the longitudinal axis of the tube, and a second open end having a pair of independent wings or ears for longitudinally splitting apart the first and second halves of the frangible tube. When the introducer is mounted over the dilator, the front end of the introducer is disposed proximate the rear of the tapered, acicular end portion of the dilator.

As the dilator is inserted into a patient's tissue, it operates to delicately spread apart (dilate) the tissue surrounding the entry hole formed by the hollow needle during the gastral insertion of the "J"-wire, thereby allowing the relatively large diameter introducer to pass through the entry hole with a minimum degree of resultant tissue trauma or damage.

Although currently available dilator/introducer devices generally provide a minimally acceptable level of performance, the devices exhibit a plethora of deficiencies when utilized during a percutaneous gastrostomy procedure.

One of the most serious problems associated with conventional dilator/introducer devices is the tendency of the first and second halves of the frangible introducer to prematurely split apart as the dilator/introducer is initially inserted into a patient. Depending upon the degree of premature, longitudinal separation, the surgeon may be required to remove the damaged dilator/introducer and reinsert a second, undamaged dilator/introducer into the patient, before continuing with the percutaneous gastrostomy procedure. As should be readily apparent, the reinsertion of a second dilator/introducer may result in additional, unwanted, deleterious tissue damage at the puncture site, potentially increasing the duration of the healing process and/or increasing the risk of postoperative infection.

The dilator utilized in many currently available dilator/introducer devices includes an opening, proximate the pair of wings on the introducer, for receiving the "J"-wire therethrough during a percutaneous gastrostomy procedure. Unfortunately, the location of the "J"-wire prevents the surgeon from securely and comfortably grasping the dilator/introducer device during percutaneous insertion. Further, the surgeon generally cannot apply force directly against the end of the dilator without inadvertently crimping the "J"-wire, rendering it useless. As such, the device must be awkwardly gripped only along its sides during insertion, potentially resulting in a less secure grip, hand slippage or a loss of control during insertion.

U.S. Pat. No. 5,139,486 to Moss, incorporated herein by reference, discloses an improved dilator/introducer device which avoids, at least to a limited degree, the above-described deficiencies associated with the operational orientation of the "J"-wire, by modifying the rearward end of the dilator to facilitate the handling of the dilator/introducer. Specifically, a longitudinal slot is formed through one side of the rearward end of the dilator to allow the "J"-wire to unobtrusively exit from the longitudinally extending central bore of the dilator. As such, a surgeon is able to apply direct pressure against the rear face of the dilator without damaging the "J"-wire. Advantageously, the incorporation of the longitudinal slot improves directional stability and force transfer during the insertion process, and reduces the probability of slippage.

Although the improved dilator/introducer device disclosed in U.S. Pat. No. 5,139,486 to Moss has proven to be a significant step forward in the art, it is deficient in several respects. First, during a percutaneous gastrostomy procedure, the surgeon is required to manually direct the end of the "J"-wire through the longitudinal slot disposed in the rearward end of the dilator. During such a manual manipulation, the surgeon may inadvertently bend the "J"-wire, potentially rendering it unsuitable for the next stage of the percutaneous gastrostomy procedure. Second, the surgeon is required to manually insert an optional plug into the rearward open end of the slotted dilator to not only prevent the "J"-wire from exiting through the rear face of the dilator where it may be damaged, but also to provide an increased surface area at the end of the dilator for the surgeon to push against during the insertion process.

SUMMARY OF THE INVENTION

In order to avoid the disadvantages of the prior art, the present invention provides an improved dilator/introducer apparatus which is designed to prevent the premature longitudinal separation of the first and second halves of the introducer.

In accordance with a preferred embodiment of the present invention, the dilator includes an enlarged end portion incorporating a pair of locking tabs which are adapted to be operationally inserted within corresponding locking slots disposed within a winged, first end of the introducer. When the locking tabs on the first end of the dilator are inserted within the introducer locking slots during the insertion of the dilator/introducer apparatus into a patient, the first and second halves of the introducer will not separate, thereby eliminating the unwanted premature longitudinal separation commonly experienced by prior art dilator/introducer devices.

The dilator of the present invention includes a unique arrangement of longitudinally extending channels for directing a "J"-wire along the length of the dilator. A ramp is provided at the end of each channel proximate the enlarged end portion of the dilator to direct an inserted "J"-wire laterally away from the dilator/introducer apparatus. Advantageously, by directing the "J"-wire away from the enlarged head of the dilator, which is designed to be operationally positioned within the palm of a surgeon during the insertion of the dilator/introducer apparatus, the "J"-wire will not be crimped or otherwise damaged.

BRIEF DESCRIPTION OF THE DRAWINGS

These and other features of the present invention will become readily apparent upon reading the following detailed description and upon reference to the drawings in which:

FIG. 1 illustrates an improved dilator/introducer apparatus in accordance with a preferred embodiment of the present invention, wherein the dilator is inserted and lockably engaged within the introducer;

FIG. 2 illustrates the dilator of the dilator/introducer apparatus of FIG. 1;

FIG. 3 is a cross-sectional view of the dilator/introducer apparatus taken along line 3—3 of FIG. 1;

FIG. 4 is a cross-sectional view of the dilator taken along line 4—4 of FIG. 2;

FIG. 8 is a partial enlarged view of a dilator/introducer apparatus in accordance with an alternate embodiment of the present invention, wherein the dilator includes a plurality of tabs for externally engaging complementary flanges on the introducer;

FIG. 9 is a cross-sectional view of the dilator/introducer apparatus taken along 9—9 of FIG. 8; and FIG. 10 is a partial perspective view of the enlarged end portion of the dilator illustrated in FIG. 8.

DETAILED DESCRIPTION OF THE INVENTION

Figure 5:
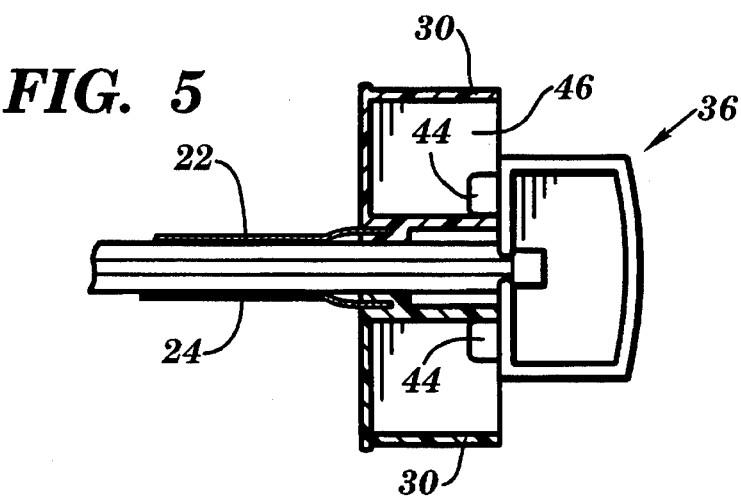
FIG. 5 is a partially cut-away view of the dilator/introducer apparatus illustrating the locking operation provided by the locking tabs of the dilator when inserted into the complementary locking slots of the introducer, wherein the locking operation prevents the premature longitudinal separation of the first and second halves of the introducer.

Referring now to the drawings, there is illustrated a dilator/introducer apparatus, generally designated as 10, in accordance with a preferred embodiment of the present invention, wherein like reference numerals refer to like components throughout the drawings.

The dilator/introducer apparatus 10 of the present invention includes a tubular, elongated, frangible introducer 12, and an elongated, needle shaped dilator 14 removably and lockably housed within the introducer 12. The dilator 14 has a tapered, needle-like tip 16 which functions to gradually spread apart the tissue layers 18 of a patient as the dilator/introducer apparatus 10 is percutaneously inserted. This is most clearly illustrated in FIG. 1, where the tissue layers 18 have been dilated by the tip 16 of the dilator 14. As known in the art, the dilator/introducer apparatus 10 is guided into the patient along a previously inserted "J"-wire 20.

The tubular, elongated, frangible introducer 12 includes first and second longitudinally separable halves 22, 24, preferably formed of metal, which are designed to be laterally separated along a pair of symmetrically disposed, longitudinal grooves 26 (only one of which is shown). The introducer 12 includes a first end having an opening 28 which is perpendicular to the longitudinal axis of the introducer, and a second, opposing end having a pair of enlarged wings 30 suitably secured to the first and second halves 22, 24 of the introducer. Of course, the enlarged wings 30 may be suitably secured to the first and second halves 22, 24 of the introducer 12 in any manner known in the art. When the dilator 14 is operationally inserted within the introducer 12, the opening 28 in the first end of the introducer is positioned slightly behind the tapered, needle-like tip 16 of the dilator 14.

The dilator 14 of the present invention includes a tapered, needle-like tip 16 having a central bore 32 for receiving the "J"-wire 20 therethrough, a center section incorporating a pair of opposing guide channels 34, 34' for guiding an inserted "J"-wire, exiting the central bore 32, along the length of the assembled dilator/introducer apparatus 10 (FIG. 1), and an enlarged end portion 36. Preferably, the enlarged end portion 36 of the dilator 14 includes a slightly convex, large surface area rear face 37 which is sized to fit within an operator's palm, thereby allowing the operator to apply direct pressure against the rear face 37 of the dilator 14 during the insertion of the dilator/introducer apparatus 10 into a patient.

As the dilator/introducer apparatus 10 is displaced along the "J"-wire 20 during the percutaneous insertion procedure, the "J"-wire exits the central bore 32 and passes into an opening 38 disposed on a first end of the center section of the dilator 14 (FIGS. 2 and 4). Thereafter, the end of the "J"-wire encounters a rounded projection 40 and is directed into one of the exposed guide channels 34, 34' extending along the length of the central section of the dilator 14. Upon reaching the enlarged end portion 36 of the dilator 14, the "J"-wire is directed laterally away from the dilator/introducer apparatus 10, where it is less likely to be crimped or otherwise damaged as the dilator/introducer apparatus 10 is inserted into a patient, by a strategically positioned ramp 42, 42'.

The enlarged end portion 36 of the dilator 14 includes a pair of locking tabs 44 which are designed to be removably inserted within a pair of complementary locking slots 46 disposed within the pair of enlarged wings 30 secured to the first and second halves 22, 24 of the introducer 12. When the locking tabs 44 are suitably inserted within the locking slots 46 as shown in FIGS. 1, 3 and 5, the first and second halves 22, 24 of the introducer 12 are prevented from separating. Further, to eliminate any lateral separation of the wings 30, a proximal side of each locking tab 44 is positioned to engage a proximal side of a respective one of the locking slots 46.

Upon removal of the locking tabs 44 from the locking slots 46 in the pair of enlarged wings 30, the first and second halves 22, 24 of the introducer 12 may be separated by applying an appropriate lateral force to each of the enlarged wings 30 of the introducer 12. The longitudinal separation of the first and second halves 22, 24 of the introducer 12, after removal of the dilator 14 from the introducer 12 is most clearly shown in FIG. 6, wherein the lateral force required for separation is illustrated by directional arrows 48.

The enlarged wings 30 include an outwardly flanged lip 50, disposed adjacent the first and second halves 22, 24 of the introducer 12, which facilitates the grasping of the dilator/introducer apparatus 10 during insertion into a patient. Further, the enlarged wings 30 are provided with a plurality of ribs 52. Preferably, the ribs 52 are formed parallel to the longitudinal axis of the dilator/introducer apparatus 10, thereby facilitating the lateral separation of the enlarged wings 30 during the separation of the first and second halves 22, 24 of the introducer.

During the intermediate stages of a percutaneous gastrostomy procedure, one end of a previously inserted "J"-wire extends outwardly from a patient's body from a small puncture site in the abdomen proximate the stomach. As known in the art, the front curved portion of the inserted "J"-wire is located within the gastrointestinal tract of the patient. At this point in the gastrostomy procedure, prior to the placement of a gastrostomy tube into the patient, the dilator/introducer apparatus 10 of the instant invention is inserted into the patient along the "J"-wire 20.

The dilator/introducer apparatus 10 is assembled by inserting the dilator 14 within the introducer 12 until the pair of locking tabs 44 formed on the enlarged end portion 36 of the dilator 14 are fully seated within the complementary locking slots 46 disposed within the end of the enlarged wings 30 of the introducer 12. When the dilator 14 is completely inserted within the introducer 12, the locking action provided by the locking tabs 44 and locking slots 46 prevents the first and second halves 22, 24 of the introducer 12 from separating when the dilator/introducer apparatus 10 is subsequently inserted into the patient. As illustrated in FIG. 1, when the dilator/introducer apparatus 10 is fully assembled, the tip 16 of the dilator 14 extends slightly beyond the opening 28 in the first end of the introducer 12.

Next, the exposed end of the "J"-wire is inserted into and through the central bore 32 in the tip 16 of the dilator 14, eventually passing into the opening 38 located in the center section of the dilator 14. Thereafter, the end of the "J"-wire is directed by the rounded projection 40 into one of the guide channels 34, 34' extending along the length of the center section of the dilator 14. Finally, the "J"-wire passes out of one of the guide channels 34, 34' and is diverted laterally away from the dilator/introducer apparatus 10 by ramps 42 or 42', respectively. Upon successful insertion of the "J"-wire, the dilator/introducer apparatus 10 is maneuvered along the "J"-wire until the tip 16 of the dilator 14 is proximate the puncture site in the patient's abdomen.

When the dilator/introducer apparatus 10 is suitably positioned over the puncture site, the enlarged end portion 36 of the dilator 14 is placed within the palm of an operator, and direct pressure is applied thereagainst, thereby inserting the tip 16 of the dilator 14 through the puncture site and tissue layers 18, into the patient's stomach. The operator continues to insert the dilator/introducer apparatus 10 until the tip 16 of the dilator 14 is appropriately positioned within the gastrointestinal tract of the patient. Since the "J"-wire is automatically directed away from the enlarged end portion 36 of the dilator 14 by ramps 42 or 42', it is not damaged or otherwise affected by the insertion procedure. Further, the first and second halves 22, 24 of the introducer 12 do not separate prematurely, as is commonly the case with prior art dilator/introducer devices, due to the coupling action provided by the interaction of the locking tabs 44 and the locking slots 46.

The dilator 14 is subsequently removed from the introducer 12 and pulled off the exposed end of the "J"-wire 20, uncoupling the locking tabs 44 and the locking slots 46, while the introducer 12 and "J"-wire are held in position.

Figure 6:
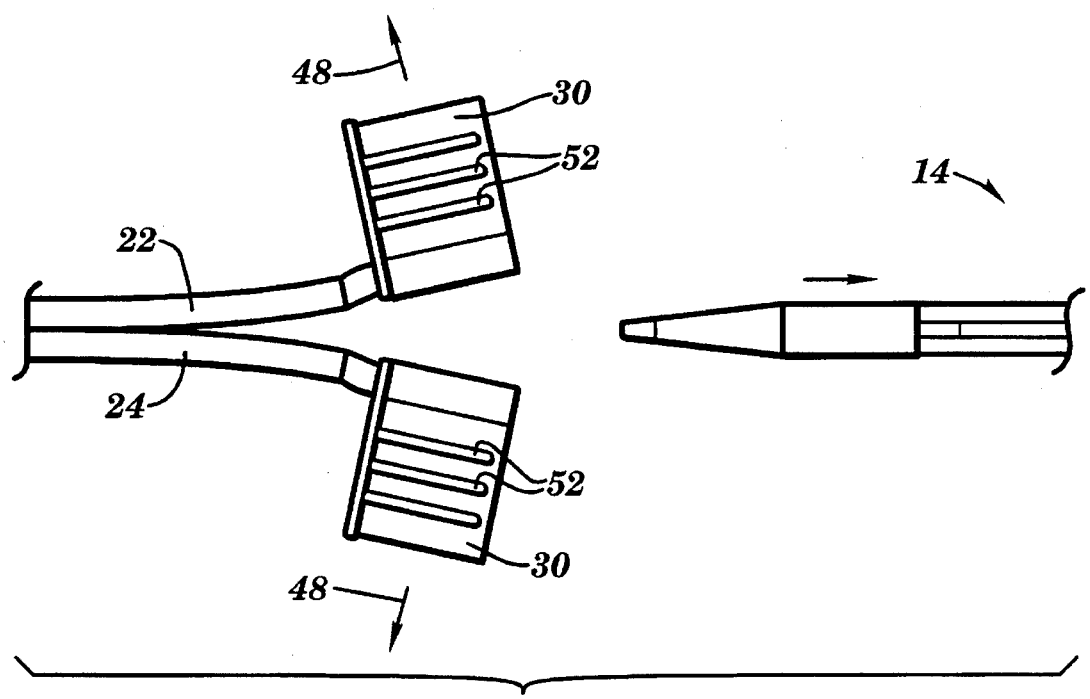
FIG. 6 illustrates the longitudinal separation of the first and second halves of the introducer subsequent to the removal of the dilator therefrom.
Figure 7:
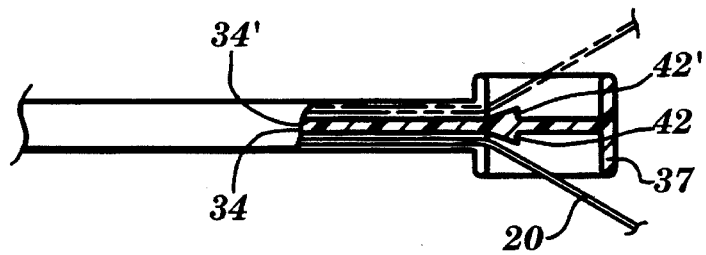
FIG. 7 is a cross-sectional view of the dilator taken along line 7—7 of FIG. 2.

A gastrostomy tube is inserted through the now empty introducer 12 by threading it along the "J"-wire 20 to its proper operational position within the gastrointestinal tract of the patient. Once the gastrostomy tube has been successfully positioned, the introducer 12 is eased out of the patient's body, where it encircles an external portion of the gastrostomy tube. To remove the introducer 12 from about the gastrostomy tube, appropriate lateral pressure is applied to the enlarged wings 30, thereby causing a longitudinal separation of the first and second halves 22, 24 of the introducer along the pair of longitudinal grooves 26 (FIG. 6). Upon complete separation, the first and second halves 22, 24 of the introducer are discarded.

A second embodiment of the dilator/introducer apparatus locking system is illustrated in FIGS. 8 through 10. Specifically, the enlarged end portion 36 of the dilator 14 includes a plurality of locking tabs 60 which are designed to engage a corresponding number of complementary slots 62 formed on opposing sides of the enlarged wings 30 of the introducer 12. As previously described, the locking system is preferably designed so that a proximal side of each locking tab 60 is positioned to engage a proximal side of a respective one of the locking slots 62 (FIG. 9), thereby preventing any lateral separation of the wings 30 as the dilator/introducer apparatus is inserted into a patient. Of course, other types of locking protuberances and complementary locking apertures may be utilized in accordance with the present invention.

The foregoing description of the preferred embodiments of the invention has been presented for purposes of illustration and description. It is not intended to be exhaustive or to limit the invention to the precise form disclosed, and obviously many modifications and variations are possible in light of the above teaching. Such modifications and variations that may be apparent to a person skilled in the art are intended to be included within the scope of this invention as defined by the accompanying claims.

I claim:

1. A dilator/introducer apparatus comprising:

a tubular introducer having first and second open ends and first and second longitudinally separable sections, each of said first and second longitudinally separable sections including a wing proximate said first open end of said tubular introducer, each wing having at least one locking aperture positioned in a rear face thereof;

a dilator having a needle shaped first end portion and an enlarged second end portion, said second end portion of said dilator including at least one locking protuberance extending from a front face thereof, wherein upon insertion of said needle shaped first end portion of said dilator into said first open end of said tubular introducer, said at least one locking protuberance is inserted into a complementary said at least one locking apertures in said wing of said introducer, said first and second longitudinally separable sections of said introducer are prevented from laterally separating.

2. The dilator/introducer apparatus according to claim 1, wherein, upon insertion of said at least one locking protuberances of said dilator into said complementary at least one locking apertures in the wings of said tubular introducer, a proximal side of each locking protuberance frictionally engages a proximal side of said complementary locking aperture.

3. The dilator/introducer apparatus according to claim 1, wherein said introducer has a longitudinal axis, and wherein the locking apertures in each wing comprise an elongate slot, an each locking protuberance is complementarily shaped for insertion into a respective one of said elongated slots, said elongate slots and said locking protuberances positioned substantially perpendicular to the longitudinal axis of said introducer.

4. A dilator/introducer apparatus comprising:

a tubular introducer having first and second open ends and first and second longitudinally separable sections, each of said first and second longitudinally separable sections including a wing proximate said first open end of said tubular introducer, each wing having at least one elongate locking aperture positioned substantially perpendicular to the longitudinal axis of the introducer, and in a rear face thereof;

a dilator having a needle shaped first end portion and an enlarged second end portion, said second end portion of said dilator including at least one elongate locking protuberance extending from a front face thereof and positioned to complement said at least one elongate locking aperture in said introducer, wherein upon insertion of said needle shaped first end portion of said dilator into said first open end of said tubular introducer, said at least one elongate locking protuberance is inserted into a complementary said at least one locking aperture in said wing of said introducer, and a proximal side of each locking protuberance frictionally engages a proximal side of said complementary locking aperture and said first and second longitudinally separable sections of said introducer are prevented from laterally separating.

* * * * *